US00PP20644P2

(12) United States Plant Patent
Hofmann

(10) Patent No.: US PP20,644 P2
(45) Date of Patent: Jan. 12, 2010

(54) ***MANDEVILLA* PLANT NAMED 'FISRIX PINKA'**

(50) Latin Name: *Mandevilla sanderi (Hemsl.) Woodson*
Varietal Denomination: Fisrix Pinka

(75) Inventor: Birgit Christa Hofmann, Rüdesheim (DE)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 12/220,039

(22) Filed: Jul. 21, 2008

(51) Int. Cl.
*A01H 5/00* (2006.01)

(52) U.S. Cl. ..... Plt./232
(58) Field of Classification Search ..... Plt./232
See application file for complete search history.

(56) References Cited

U.S. PATENT DOCUMENTS

PP9,117 P * 4/1995 Christensen ..... Plt./232
PP15,539 P2 * 2/2005 Misato et al. ..... Plt./232

* cited by examiner

*Primary Examiner*—Susan B McCormick Ewoldt
(74) *Attorney, Agent, or Firm*—S. Matthew Edwards

(57) ABSTRACT

A new *Mandevilla* plant named 'Fisrix Pinka,' particularly distinguished by large pink flowers, floriferous habit, deep green, glossy foliage, elliptical leaves, well branched, bushy plant habit, and vigorous growth.

1 Drawing Sheet

Latin name of the genus and species of the plant claimed: *Mandevilla sanderi* (Hemsl.) Woodson.

Varietal denomination: 'Fisrix Pinka'.

BACKGROUND OF THE NEW PLANT

The present invention comprises a new and distinct cultivar of *Mandevilla*, botanically known as *Mandevilla sanderi*, and hereinafter referred to by the variety name 'Fisrix Pinka.'

'Fisrix Pinka' is a product of a planned breeding program. The new cultivar 'Fisrix Pinka' has large pink flowers, floriferous habit, deep green, glossy foliage, elliptical leaves, well branched, bushy plant habit, and vigorous growth.

'Fisrix Pinka' originated from a hybridization made in the summer of 2003 in Hillscheid, Germany. The female parent is the commercial *Mandevilla* variety offered as 'Sundaville'® Red, 'Moulin Rouge' in France, which is identical to 'Sunmandecrim,' U.S. Plant Pat. No. 15,539, having red flower color, good branching characteristics, and medium green foliage. The male parent is the commercial *Mandevilla* variety offered as 'My Fair Lady'™ and patented as 'Helle,' U.S. Plant Pat. No. 9,117 with white to pale pink flower color, deep green foliage, and relatively few branches.

The seeds produced by the hybridization were sown in the fall of 2003. The resulting seedlings (plants) were evaluated in late summer to fall of 2004. 'Fisrix Pinka' was selected as one flowering plant in a greenhouse in Hillscheid, Germany.

The plant was propagated asexually for the first time in the fall of 2004. It has been asexually reproduced repeatedly by vegetative cuttings in Hillscheid, Germany over a 2–3 year period. Horticultural examination of plants grown from cuttings of the plant initiated in Hillscheid, Germany, in the spring of 2005, and continuing thereafter, has demonstrated that the combination of characteristics as herein disclosed for 'Fisrix Pinka' are firmly fixed and are retained through successive generations of asexual reproduction.

Plant Breeder's Rights for 'Fisrix Pinka' were applied for in Europe on Dec. 13, 2006 and in Canada on Jan. 28, 2008.

'Fisrix Pinka' has not been made publicly available more than one year prior to the filing of this application.

DESCRIPTION OF THE PHOTOGRAPH

This new *Mandevilla* plant is illustrated by the accompanying photograph which shows blooms, buds, and foliage of the plant in full color. The colors shown are as true as can be reasonably obtained by conventional photographic procedures. The photograph is of an about 12 month old plant grown in a greenhouse.

DETAILED BOTANICAL DESCRIPTION

The following detailed descriptions set forth the distinctive characteristics of 'Fisrix Pinka.' The data which define these characteristics were collected from asexual reproductions carried out in Hillscheid, Germany. The plant history was taken in early June 2007 on 9 month old plants, planted in late August to early September 2006, pinched once, and grown in 12 cm diameter pots/containers in a glass-covered greenhouse with additional light during the winter months.

Color readings were taken under natural light. Color references are primarily to the R.H.S. Colour Chart of The Royal Horticultural Society of London (R.H.S.) (2001 edition). Texture description details were observed under a magnifying glass.

BRIEF SUMMARY OF INVENTION

The following are the most outstanding and distinguishing characteristics of this new cultivar when grown under normal horticultural practices in Hillscheid, Germany.

1. Large, medium pink colored flowers with relatively wide petals
2. Floriferous with inflorescences of 5–6 flowers each
3. Deep green foliage with elliptical leaves and glossy surface 4. Vigorous growth habit; well-branching
5. Upright to spreading, bushy plant habit

COMPARISON WITH PARENTAL AND COMMERCIAL CULTIVARS

'Fisrix Pinka' differs from the female parent, *Mandevilla* plant 'Sunmandecrim,' U.S. Plant Pat. No. 15,539, in that 'Fisrix Pinka' has a pink flower color, while 'Sunmandecrim' has a (deep) red flower color and somewhat less deep foliage color.

'Fisrix Pinka' differs from the male parent, the commercial *Mandevilla* plant 'Helle,' U.S. Plant Pat. No. 9,117, in that 'Fisrix Pinka' has much deeper pink colored flowers, while 'Helle' has a white to pale pink hue and light pink buds. Additionally, 'Fisrix Pinka' develops more branches, and foliage is more elongate (elliptic) than with 'Helle', that has ovate to nearly round leaves.

'Fisrix Pinka' differs from the commercial cultivar Cosmos Pink/'Sunmandecos' (U.S. Plant Pat. No. 15,202) in that 'Fisrix Pinka' has a more uniform pink flower without any distinct white pattern in the center of the flower, not quite as large flowers, earlier flowering in spring and comparatively little tendency to developing vines.

DESCRIPTION OF THE PLANT

Classification:
- *Family.*—Apocynaceae.
- *Botanical name.*—*Mandevilla sanderi* (Hemsl.) Woodson.

Parentage:
- *Female parent.*—'Sunmandecrim', a commercial red-colored *Mandevilla* plant (U.S. Plant Pat. No. 15,539).
- *Male parent.*—'Helle', a commercial, pale pink flowered *Mandevilla* plant (U.S. Plant Pat. No. 9,117).

Whole plant:
- *Form and growth habit.*—Perennial or sub-shrub with herbaceous younger stems and vines, and woody bases, initially upright, develops vines mainly during winter months at low light conditions; commercially mostly grown as an annual plant.
- *Height.*—41 cm (from top of soil) for 9 month old plants.
- *Width.*—Approximately 40 cm (35–45 cm) foliage canopy, respective 52 cm width including inflorescences.
- *Time to produce a finished flowering plant.*—About 5 months for a small flowering plant in a 12 cm pot in winter through spring cultivation.
- *Plant use and outdoor plant performance.*—For flowering pots and for larger containers (best with support), or outdoors in a flower bed, good heat and drought tolerance.
- *Time to initiate and develop roots.*—About 25 days.
- *Root description.*—Fibrous, a little fleshy, and freely branching.

Stems:
- *Number of (main) branches.*—9–11, one (on average) of which is a vine.
- *Length.*—30–40 cm without the inflorescence (excluding vines).
- *Diameter.*—3–4 mm as measured in the middle.
- *Internode length.*—2.0–4.0 cm.
- *Color.*—Mainly RHS 143B, grass green, no anthocyanin; wooden base: RHS 177C, brown.
- *Texture.*—Woody at the base, smooth in the upper part, glabrous.

Leaves:
- *Arrangement.*—Usually opposite.
- *Shape.*—Elliptical.
- *Apex.*—Acuminate.
- *Base.*—Rounded or truncate, may even appear weakly cordate.
- *Margin.*—Entire.
- *Length.*—6.4–7.2 cm.
- *Width.*—4.8–5.5 cm.
- *Color young foliage.*—Upper surface: RHS 143B. Lower surface: RHS 144B.
- *Leaf vein color.*—Upper surface reddish, RHS 181B (reddish color fades and disappears with maturing).
- *Color mature (fully expanded).*—Upper surface: RHS 137B to 137C. Lower surface: More yellowish green than RHS 138B, or between RHS 138B and RHS 144B.
- *Venation.*—Pinnate.
- *Venation color.*—Upper surface indistinct, same as leaf color; lower surface midrib RHS 145B, side veins are very fine, near RHS 138B.
- *Leaf texture.*—Leathery, smooth, glabrous (both sides), glossy.
- *Petiole length.*—Approximately 1.0–1.3 cm.
- *Petiole width.*—2–3 mm.
- *Petiole color.*—Grass green, RHS 143C with mature leaves; young leaves: reddish, RHS 181B, reddish hue fades and disappears with age.

Flower bud: Elongated, spindle shape.
- *Diameter.*—About 1.4 cm.
- *Length.*—Up to 7.5 cm.
- *Color (at tight bud).*—Upper part: rose red, RHS 58B; lower part is mostly pale green, RHS 145C to 145D.

Inflorescence:
- *Inflorescence type.*—Raceme, emerging at the nodes, with the flowers in an alternate arrangement.
- *Blooming habit.*—Continuously through the summer months.
- *Quantity of inflorescences per plant.*—Mostly 14–18.
- *Lastingness of individual flowers on the plant.*—8–10 days.
- *Fragrance.*—None.
- *Inflorescence length.*—Approximately 15 cm (including peduncle).
- *Number of flowers per inflorescence.*—Most often 5–6 in various stages of development.

Peduncle:
- *Color.*—Light green, RHS 143B.
- *Length.*—5–7 cm, somewhat variable.
- *Diameter.*—About 2 mm.
- *Texture.*—Smooth, glabrous, somewhat glossy.

Flower:
- *Type.*—Single.
- *Shape.*—Lower part of corolla is tube to funnel shaped formed by the fused petals, petal lobes open outwards in a star-shape, at approx. rights angels and slightly overlapping.
- *Corolla length.*—6–5–7 cm.
- *Corolla diameter (flower 'face').*—8–9 cm.
- *Diameter of funnel at opening.*—Approximately 2.0 cm.
- *Color upper surface.*—Initially between RHS 58B and 58C, turns to RHS 67D or 68B later.
- *Color lower surface.*—Deep pink, RHS 63B to 64D.

*Color funnel, inside.*—Deep yellow, RHS 13A.

*Color funnel, outside.*—Upper part light pink, RHS 62B, lower part pale yellow to cream, RHS 4D or 154D (pale yellow-green).

Petals: 5, lower parts fused, free lobes are roughly ovate to triangular, asymmetric, with the right part of the petal blade much wider than the left one.

*Apex.*—Acute.

*Base.*—Fused.

*Margin.*—Entire, occasionally a little crenulate in parts.

*Texture.*—Smooth.

*Length* (*from the corolla opening*).—4.2–4.7 cm.

*Width, maximum.*—3.5–4.0 cm.

Calyx: 5 sepals, closely attached to the base of the flower.

*Color.*—Visible (outer) surface: pale green, RHS 145A, a little anthocyanin at the tips, RHS 57A.

*Length.*—7–10 mm.

*Width.*—1–2 mm.

*Shape.*—Ligulate.

*Apex.*—Acute, almost spine-like, yet soft.

*Base.*—Fused.

*Texture.*—Glabrous.

Pedicels:

*Color.*—Dull green, RHS 146C, often partly infused with anthocyanin: RHS 176D, brown.

*Length.*—1.1–1.4 cm.

*Diameter.*—2 mm.

*Texture.*—Smooth, glabrous.

Reproductive organs:

*Stamens.*—5, connivent, at the base of the corolla funnel.

*Filament.*—Fused with the base of the flower.

*Anther.*—Elongate, 2 thecae, 8–10 mm in length.

*Color.*—Light yellow orange, RHS 20C.

*Pollen amount.*—Moderate.

*Pollen color.*—RHS 11D.

*Pistil.*—One, 5 lobed stigma.

*Length.*—2.0–2.3 cm, 0.1 cm in diameter.

*Stigma color.*—RHS 150D.

*Style color.*—RHS 150B.

Fruit and seed set: Spontaneous seed set has not been observed to date.

Disease/pest resistance: Disease resistance and/or susceptibility has not been observed to date.

What is claimed is:

1. A new and distinct variety of *Mandevilla* plant named 'Fisrix Pinka,' substantially as illustrated and described herein.

* * * * *

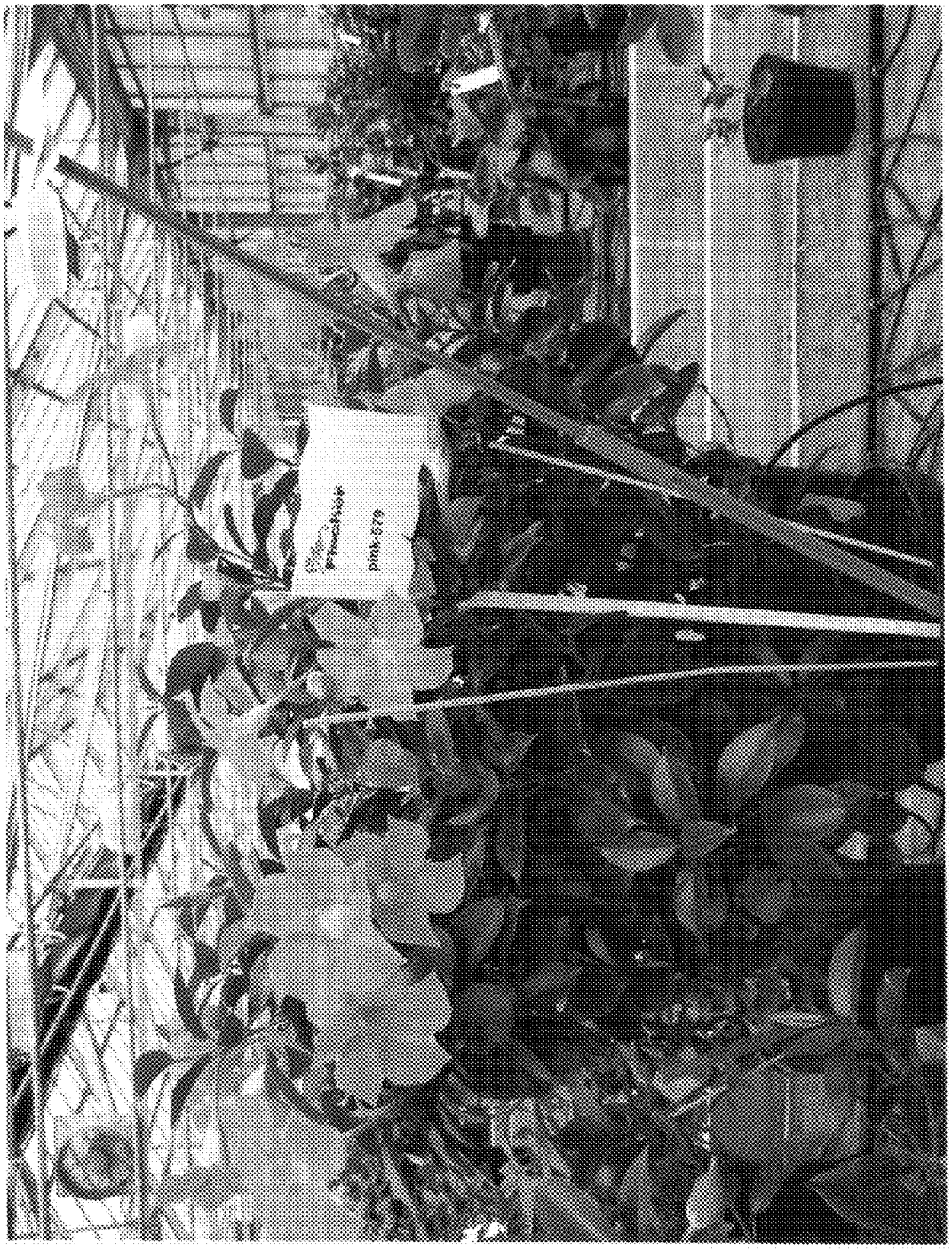
pink-379

UNITED STATES PATENT AND TRADEMARK OFFICE

CERTIFICATE OF CORRECTION

PATENT NO. : PP 20,644 P2
APPLICATION NO. : 12/220039
DATED : January 12, 2010
INVENTOR(S) : Hofmann It is certified that error appears in the above-identified patent and that said Letters Patent is hereby corrected as shown below:

At column 4, line 58, delete "rights angels" and insert therefor --right angles--

At column 4, line 60, delete "6-5" and insert therefor --6.5--

Signed and Sealed this

Second Day of March, 2010

David J. Kappos

David J. Kappos
*Director of the United States Patent and Trademark Office*